United States Patent
Welch et al.

(10) Patent No.: US 6,436,675 B1
(45) Date of Patent: Aug. 20, 2002

(54) USE OF CODON-VARIED OLIGONUCLEOTIDE SYNTHESIS FOR SYNTHETIC SHUFFLING

(75) Inventors: Mark Welch, Fremont; Jon Ness, Sunnyvale; Claes Gustafsson, Belmont; Willem P. C. Stemmer, Los Gatos; Jeremy Minshull, Menlo Park, all of CA (US)

(73) Assignee: Maxygen, Inc., Redwood City, CA (US)

( * ) Notice: Subject to any disclaimer, the term of this patent is extended or adjusted under 35 U.S.C. 154(b) by 0 days.

(21) Appl. No.: 09/408,393

(22) Filed: Sep. 28, 1999

(51) Int. Cl.[7] ............................. C12Q 1/68; C12P 19/34; C07H 21/00

(52) U.S. Cl. ........................ 435/91.1; 435/6; 536/25.3

(58) Field of Search ................... 435/6, 91.1; 536/25.3

(56) References Cited

U.S. PATENT DOCUMENTS

| | | |
|---|---|---|
| 5,264,563 A | 11/1993 | Huse |
| 5,512,463 A | 4/1996 | Stemmer |
| 5,514,588 A | 5/1996 | Varadaraj |
| 5,605,793 A | 2/1997 | Stemmer |
| 5,717,085 A | 2/1998 | Lyttle et al. |
| 5,763,239 A | 6/1998 | Short et al. |
| 5,789,228 A | 8/1998 | Lam et al. |
| 5,789,577 A | 8/1998 | Geysen |
| 5,811,238 A | 9/1998 | Stemmer et al. |
| 5,814,473 A | 9/1998 | Warren et al. |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minushull et al. |
| 5,869,644 A | 2/1999 | Shortle et al. |
| 5,876,997 A | 3/1999 | Kretz |
| 5,925,749 A | 7/1999 | Mathur et al. |
| 5,928,905 A | 7/1999 | Stemmer et al. |
| 5,939,250 A | 8/1999 | Short |
| 5,939,300 A | 8/1999 | Robertson et al. |
| 5,942,430 A | 8/1999 | Robertson et al. |
| 5,948,666 A | 9/1999 | Callen et al. |
| 5,958,672 A | 9/1999 | Short |
| 5,958,751 A | 9/1999 | Murphy et al. |
| 5,962,258 A | 10/1999 | Mathur et al. |
| 5,962,283 A | 10/1999 | Warren et al. |
| 5,965,405 A | 10/1999 | Winter et al. |
| 5,965,408 A | 10/1999 | Short |
| 5,985,646 A | 11/1999 | Murphy et al. |
| 6,171,820 B1 | 1/2001 | Short |

FOREIGN PATENT DOCUMENTS

| | | |
|---|---|---|
| EP | 0911396 A2 | 4/1999 |
| EP | 0911396 A3 | 5/1999 |
| EP | 0934999 A1 | 8/1999 |
| WO | WO 91/06643 | 5/1991 |
| WO | WO 92/06176 | 4/1992 |
| WO | WO 95/22625 | 8/1995 |
| WO | WO 96/16073 | 5/1996 |
| WO | WO 96/33207 | 10/1996 |
| WO | WO 97/07205 | 2/1997 |
| WO | WO 97/20078 | 6/1997 |
| WO | WO 97/25410 | 7/1997 |
| WO | WO 97/33957 | 9/1997 |
| WO | WO 97/35957 | 10/1997 |
| WO | WO 97/35966 | 10/1997 |
| WO | WO 97/44361 | 11/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |

(List continued on next page.)

OTHER PUBLICATIONS

Kim et al. (1997) "Codon Optimization for High–level Expression of Human Erythropoietin (EPO) in Mammalian Cells." *Gene* 199(1–2):293–300–1.

Carter et al. (1985) "Improved oligonucleotide site directed mutagenesis using M13 vectors" *Nucleic Acids Res.* 13, 4431–4443.

Kayushin, A. L. et al., (1996) *Nucleic Acids Res.*, 24, 3748–3755.

Ling et al. (1997) "Approaches to DNA mutagenesis: an overview" *Anal Biochem.*, Dec. 15;254(2):157–78.

Nakamaye & Eckstein (1986) "Inhibition of restriction endonuclease Nci I cleavage by phosphorothioate groups and its application to oligonucleotide–directed mutagenesis." *Nucleic Acids Res._*14:9679–9698.

Sayers et al. (1988) "5'–3' Strand specific cleavage of phosphorothioate–containing DNA by reaction with restriction endonucleases in the presence of ethidium bromide" *Nucleic Acids Res.* 16:803–814.

Sayers et al. (1988). "Y–T Exonucleases in phosphorothioate–based oligonucleotide–directed mutagenesis." *Nucleic Acids Res._*16:791–802;.

Smith (1985) "In vitro mutagenesis" *Ann. Rev. Genet.*, 19:423–462.

Taylor et al. (1985) "The rapid generation of oligonucleotide–directed mutations at high frequency using phosphorothioate–modified DNA" *Nucleic Acids Res.* 13:8765–8787.

(List continued on next page.)

Primary Examiner—John S. Brusca
Assistant Examiner—Young Kim
(74) Attorney, Agent, or Firm—Norman J. Kruse; Christopher C. Sappenfield; Quine Intellectual Property Law Group, P.C.

(57) ABSTRACT

Methods of providing shuffling libraries that include codon-varied oligonucleotide sequences are described. Codon-varied oligonucleotides are synthesized using trinucleotide or mononucleotide phosphoramidite sequences, and are derived from homologous or non-homologous nucleic acid sequences, or combinations of such sequences. Various methods of recombining codon-varied oligonucleotide sequences to expedite artificial evolution are also described. The present invention additionally relates to various integrated systems that are optionally used to automate these recombination methods.

39 Claims, 1 Drawing Sheet

FOREIGN PATENT DOCUMENTS

| | | |
|---|---|---|
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/28416 | 7/1998 |
| WO | WO 98/31837 | 7/1998 |
| WO | WO 98/36080 | 8/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/48034 | 10/1998 |
| WO | WO 98/58085 | 12/1998 |
| WO | WO 99/07837 | 2/1999 |
| WO | WO 99/08539 | 2/1999 |
| WO | WO 99/10472 | 3/1999 |
| WO | WO 99/10539 | 3/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO 99/57128 | 11/1999 |
| WO | WO 99/65927 | 12/1999 |

OTHER PUBLICATIONS

Taylor et al. (1985) "The use of phosphorothioate–modified DNA in restriction enzyme reactions to prepare nicked DNA." *Nucleic Acids Res.* 13:8749–8764.

Virnekäs, B., et al., (1994) *Nucleic Acids Res.*, 22, 5600–5607.

Wells (1986) "Importance of hydrogen bond formation in stabilizing the transition state of subtilisin." *Trans. R. Soc. Lond.* A317, 415–423.

Dale et al. (1996) "Oligonucleotide–directed random mutagenesis using the phosphorothioate method" *Methods Mol Biol.*, 57:369–74.

Glaser et al., (1992) *J. Immunol.*, 149, 3903–3913.

Altschul et al., *J. Mol. Biol.* 215:403–410 (1990).

Carter (1987) "Improved oligonucleotide–directed mutagenesis using M13 vectors." *Methods in Enzymol.* 154:382–403.

Crameri et al., (1996), "Construction And Evolution Of Antibody–Phage Libraries By DNA Shuffling" *Nature Medicine* 2(1):100–103.

Needleman & Wunsch, *J. Mol. Biol.* 48:443 (1970).

Pearson & Lipman, *Proc. Nat'l. Acad. Sci. USA* 85:2444 (1988).

Smith & Waterman, *Adv. Appl. Math.* 2:482 (1981).

Stemmer (1994) "DNA Shuffling by Random Fragmentation and Reassembly: in vitro Recombination for Molecular Evolution," *Proc. Natl. Acad. USA* 91:10747–10751.

Stemmer et al., (1994) "Rapid Evolution of a Protein" *Nature* 370:389–391.

Chang, C., et al. (1999) "Evolution of a cytokine using DNA family shuffling." *Nature Biotechnology* 17:793–797.

Christians F.C. et al., (1999) "Directed evolution of thymidine kinase for AZT phosphorylation using DNA family shuffling." *Nature Biotechnology* 17:259–264.

Crameri et al., (1993) "10(20)–Fold aptamer library amplification without gel purification," *Nuc. Acids Res.* 21(18):4410.

Crameri, A. & Stemmer W.P.C. (1995) "Combinatorial multiple cassette mutagenesis creates all the permutations of mutant and wildtype cassettes." *Biotechniques* 18:194–195.

Crameri, A. et al. (1996) "Improved green fluorescent protein by molecular evolution using DNA shuffling." *Nature Biotechnology* 14:315–319.

Crameri, A. et al., (1997) "Molecular evolution of an arsenate detoxification pathway by DNA shuffling." *Nature Biotechnology* 15:436–438.

Crameri, A. et al., (1998) "DNA shuffling of a family of genes from diverse species accelerates directed evolution." *Nature* 391:288–291.

Gates, C.M. et al., (1996) "Affinity selective isolation of ligands from peptide libraries through display on a lac repressor headpiece dimer". *Journal of Molecular Biology* 255:373–386.

Minshull, J., Stemmer, W.P.C. (1996) "Protein evolution by molecular breeding." *Current Opinion in Chemical Biology* 3:284–290.

Ness, J. et al., (1999) "DNA shuffling of subgenominc sequences of subtilisin." *Nature Biotechnology* 17:893–896.

Patten, P.A. et al., (1997) "Application of DNA Shuffling to Pharmaceuticals and Vaccines." *Current Opinion in Biotechnology* 8:724–733.

Stemmer, W.P.C. (1995) "The Evolution of Molecular Computation." *Science* 270:1510.

Stemmer, W.P.C. (1995) "Searching Sequence Space." *Bio/Technology* 13:549–553.

Stemmer, W.P.C. (1996) "Sexual PCR and Assembly PCR." *The Encyclopedia of Molecular Biology.* VCH Publishers, New York, pp. 447–457.

Stemmer, W.P.C. & Soong, N.W. (1999) "Molecular breeding of viruses of targeting and other clinical properties." *Tumor Targeting* 4:59–62.

Zhang, J. et al., (1997) "Directed evolution of an effective fucosidase from a galactosidase by DNA shuffling and screening." *Proceedings of the National Academy of Sciences, USA* 94:4504–4509.

USE OF CODON-VARIED OLIGONUCLEOTIDE SYNTHESIS FOR SYNTHETIC SHUFFLING

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to methods of providing shuffling libraries that include codon-varied oligonucleotide sequences. Codon-varied oligonucleotides can be synthesized using trinucleotide or mononucleotide phosphoramidite sequences, and can be derived from homologous or non-homologous nucleic acid sequences, or combinations of such sequences. In turn, codon-varied oligonucleotide sequences can be utilized for recombination in various methods of artificial evolution.

BACKGROUND OF THE INVENTION

The use of trinucleotide phosphoramidites in solid-phase DNA synthesis was previously thought to be unfeasible, as only marginal yields could be achieved. Sondek, J. and Shortle, D. (1992) *J. Immunol.*, 149, 3903–3913. These poor results were attributed to the steric bulk of the trinucleotide molecules. Id. However, it has since been shown that trinucleotide phosphoramidites representing codons for all 20 amino acids can be successfully used to introduce entire codons into oligonucleotides in automated, solid-phase DNA synthesis and thus can function as excellent reagents for the synthesis of mixed oligonucleotides for random mutagenesis. Virnekäs, B., et al., (1994) *Nucleic Acids Res.*, 22, 5600–5607. Other references involving the synthesis of trinucleotide phoshoramidites, their subsequent use in oligonucleotide synthesis, and related issues are described in, e.g., Kayushin, A. L. et al., (1996) *Nucleic Acids Res.*, 24, 3748–3755, Huse, U.S. Pat. No. 5,264,563 "PROCESS FOR SYNTHESIZING OLIGONUCLEOTIDES WITH RANDOM CODONS," Lyttle et al., U.S. Pat. No. 5,717,085 "PROCESS FOR PREPARING CODON AMIDITES" Shortle et al., U.S. Pat. No. 5,869,644 "SYNTHESIS OF DIVERSE AND USEFUL COLLECTIONS OF OLIGONUCLEOTIDES," Greyson, U.S. Pat. No. 5,789,577 "METHOD FOR THE CONTROLLED SYNTHESIS OF POLYNUCLEOTIDE MIXTURES WHICH ENCODE DESIRED MIXTURES OF PEPTIDES," and Huse, WO 92/06176 "SURFACE EXPRESSION LIBRARIES OF RANDOMIZED PEPTIDES."

The inventors and their co-workers have developed various rapid artificial evolution techniques for creating improved industrial, agricultural, and therapeutic genes and encoded proteins including via oligonucleotide-mediated recombination. These methodologies and related aspects are described in a variety of sources, e.g., Stemmer et al., (1994) "Rapid Evolution of a Protein" *Nature* 370:389–391, Stemmer (1994) "DNA Shuffling by Random Fragmentation and Reassembly: in vitro Recombination for Molecular Evolution," *Proc. Natl. Acad. USA* 91:10747–10751, Crameri et al., (1996), "Construction And Evolution Of Antibody-Phage Libraries By DNA Shuffling" *Nature Medicine* 2(1):100–103, Stemmer U.S. Pat. No. 5,603,793 "METHODS FOR IN VITRO RECOMBINATION," Stemmer et al., U.S. Pat. No. 5,830,721 "DNA MUTAGENESIS BY RANDOM FRAGMENTATION AND REASSEMBLY," Stemmer et al., U.S. Pat. No. 5,811,238 "METHODS FOR GENERATING POLYNUCLEOTIDES HAVING DESIRED CHARACTERISTICS BY ITERATIVE SELECTION AND RECOMBINATION," Stemmer et al., (1998) U.S. Pat. No. 5,834,252 "End Complementary Polymerase Reaction," Minshull et al., U.S. Pat. No. 5,837,458 "Methods and Compositions for Cellular and Metabolic Engineering," and U.S. Provisional Patent Applications, Ser. Nos. 60/118,813 and 60/141,049 "Oligonucleotide Mediated Nucleic Acid Recombination," filed Feb. 5, 1999 and Jun. 24, 1999, respectively, each of which is incorporated by reference in its entirety for all purposes. Additional details regarding DNA shuffling can also be found in WO95/22625, WO97/20078, WO96/33207, WO97/33957, WO98/27230, WO97/35966, WO98/31837, WO98/13487, WO98/13485 and WO989/42832, each of which is also incorporated by reference in its entirety for all purposes.

Recently, the use of oligonucleotides for "family" shuffling was described by the inventors and their co-workers in U.S. Provisional Patent Applications, Ser. Nos. 60/118,813 and 60/141,049, supra. Additional oligonucleotide shuffling methods would be desirable. The present invention provides new codon-based oligonucleotide mediated shuffling methods and related compositions, as well as a variety of additional features which will become apparent upon review of the following description.

SUMMARY OF THE INVENTION

The present invention provides recombination methodologies in which codon-varied oligonucleotides are shuffled to provide recombined nucleic acid populations. Codon-varied oligonucleotides are synthesized, e.g., utilizing codon- or trinucleotide-based phosphoramidite coupling chemistry. This approach affords extensive flexibility to shuffling processes, as codon-varied oligonucleotides can be based upon homologous or non-homologous nucleotide sequences, or even combinations of such sequences.

In a first aspect, the present invention is directed to a method of recombining codon-varied oligonucleotides. It includes synthesizing, hybridizing, and elongating a set of overlapping codon-varied oligonucleotides to provide a population of recombined nucleic acids. In one embodiment, this method can include selecting at least first and second nucleic acids to be recombined, where the set of codon-varied oligonucleotides includes a plurality of codon-varied nucleic acids which correspond to the first and second nucleic acids. The first and second nucleic acids can be homologous or non-homologous.

In one embodiment, the sythesizing step of this method is a trinucleotide synthesis format that includes providing a substrate sequence having a 5' terminus and at least one base, both of which have protecting groups thereon. The 5' protecting group of the substrate sequence is then removed to provide a 5' deprotected substrate sequence, which is then coupled with a selected trinucleotide phosphoramidite sequence. The trinucleotide has a 3' terminus, a 5' terminus, and three bases, each of which has protecting groups thereon. The coupling step yields an extended oligonucleotide sequence. Thereafter, the removing and coupling steps are optionally repeated. When these steps are repeated, the extended oligonucleotide sequence yielded by each repeated coupling step becomes the substrate sequence of the next repeated removing step until a desired codon-varied oligonucleotide is obtained. This trinucleotide synthesis format can optionally include coupling together one or more of: mononucleotides, trinucleotide phosphoramidite sequences, and oligonucleotides.

The synthesizing step is optionally a "split-pool" synthesis format that includes providing substrate sequences, each having a 5' terminus and at least one base, both of which have protecting groups thereon. The 5' protecting groups of the substrate sequences are removed to provide 5' deprotected substrate sequences, which are then coupled with selected trinucleotide phosphoramidite sequences. Each trinucleotide has a 3' terminus, a 5' terminus, and three bases, all of which have protecting groups thereon. The coupling step yields extended oligonucleotide sequences. Thereafter, the removing and coupling steps are optionally repeated. When these steps are repeated, the extended oligonucleotide sequences yielded by each repeated coupling step become the substrate sequences of the next repeated removing step until extended intermediate oligonucleotide sequences are produced.

Additional steps of the split-pool format optionally include splitting the extended intermediate oligonucleotide sequences into two or more separate pools. After this is done, the 5' protecting groups of the extended intermediate oligonucleotide sequences are removed to provide 5' deprotected extended intermediate oligonucleotide sequences in the two or more separate pools. Following this, these 5' deprotected intermediates are coupled with one or more selected mononucleotides, trinucleotide phosphoramidite sequences, or oligonucleotides in the two or more separate pools to yield further extended intermediate oligonucleotide sequences. In turn, these further extended sequences are pooled into a single pool. Thereafter, the steps beginning with the removal of the 5' protecting groups of the substrate sequences to provide 5' deprotected substrate sequences are optionally repeated. When these steps are repeated, the further extended oligonucleotide sequences, yielded by each repeated coupling step that generates those specific sequences, become the substrate sequences of the next repeated removing step that includes those specific sequences until desired codon-varied oligonucleotides are obtained.

Both synthetic protocols described, supra, can optionally be performed in an automated synthesizer that automatically performs the steps. This aspect includes inputting character string information into the automated synthesizer corresponding to the desired codon-varied oligonucleotides to be obtained, e.g., information corresponding to two or more nucleic acids to be recombined. Additionally, the protected substrate sequences of both synthetic formats can include 3' ends that are covalently attached to a solid support.

The hybridization step of the method described herein can occur in vitro or in vivo. The elongation step of this method optionally includes providing a hybridized set of overlapping codon-varied oligonucleotides and extending one or more members of that hybridized set with a polymerase, e.g., a thermostable polymerase.

In one embodiment, the method of recombining codon-varied oligonucleotides optionally includes denaturing the population of recombined nucleic acids to provide denatured nucleic acids. These denatured nucleic acids are then re-hybridized and in turn, elongated. In another embodiment of this method, the denaturing, re-hybridizing, and elongating steps are repeated at least once and optionally twice, three times, four times, or more. Finally, the resulting elongated re-hybridized recombined nucleic acids, from either embodiment, are selected for at least one desired trait or property.

In an additional embodiment of the method in which the denaturing, re-hybridizing, and elongating steps are repeated at least once, a plurality of members of the population of recombined nucleic acids is optionally selected for a desired trait or property to provide first round selected nucleic acids. This method optionally includes hybridizing a second set of overlapping codon-varied oligonucleotides to provide a population of further recombined nucleic acids. This method also optionally includes sequencing the first round selected nucleic acids, where the second set of overlapping codon-varied oligonucleotides is derived from the first round selected nucleic acids by aligning sequences of the first round selected nucleic acids to identify regions of identity and regions of diversity. The second set of overlapping codon-varied oligonucleotides is then synthesized to include a plurality of oligonucleotides, each of which include subsequences corresponding to at least one region of diversity. The first round selected nucleic acids encode, e.g., polypeptides of about 50 amino acids or less, or larger peptides, e.g., 60, 70, 80, 90 amino acids or more. Furthermore, the second set of overlapping codon-varied oligonucleotides optionally include a plurality of oligonucleotide member types which correspond to consensus region subsequences derived from a plurality of the first round selected nucleic acids.

In another aspect, the method of recombining codon-varied oligonucleotides optionally includes selecting at least one member of the population of recombined nucleic acids for at least one desired trait or property. Also, the set of overlapping codon-varied oligonucleotides optionally includes a plurality of oligonucleotide member types that include consensus region subsequences derived from a plurality of homologous target nucleic acids. Further, the set of overlapping codon-varied oligonucleotides, including a plurality of oligonucleotide member types, includes, alternatively, at least about 3, 5, 10, 100, 1,000 or more member types. Finally, the set of overlapping codon-varied oligonucleotides optionally includes a plurality of homologous oligonucleotide member types that are present in either approximately equimolar amounts or approximately non-equimolar amounts.

In a second aspect, the invention provides a method of recombining at least two parental nucleic acids to provide at least one recombinant nucleic acid. This method includes providing a composition comprising at least one set of fragmented parental nucleic acids corresponding to the at least two parental nucleic acids. The set of fragmented parental nucleic acids includes a plurality of overlapping codon-varied oligonucleotides. Next, the composition is hybridized to provide at least one hybridized nucleic acid. The at least one hybridized nucleic acid is then elongated to provide at least one recombinant nucleic acid that comprises at least one subsequence from each of the at least two parental nucleic acids.

The set of fragmented parental nucleic acids recombined in this method are optionally partially produced by cleaving the two parental nucleic acids with a DNase enzyme. As another alternative, at least a portion of the set of fragmented parental nucleic acids are optionally produced by partial chain elongation using a polymerase, and one or both of the parental nucleic acids used as templates for elongation of one or more hybridized polymerase primer nucleic acids. Additionally, at least a portion of the set of fragmented parental nucleic acids are optionally produced by synthesizing oligonucleotides which correspond to one or more of the at least two parental nucleic acids, which oligonucleotides include a plurality of codon-varied oligonucleotides. The at least two parental nucleic acids to be recombined by this method are optionally homologous or non-homologous.

The hybridization step of this method of recombining at least two parental nucleic acids optionally includes hybridizing at least one codon-varied oligonucleotide with at least one additional overlapping codon-varied oligonucleotide to provide the at least one hybridized nucleic acid. The hybridizing step, alternatively, includes hybridizing at least one codon-varied oligonucleotide with at least one DNase fragmented parental nucleic acid to provide the at least one hybridized nucleic acid. As a further option, the hybridizing step can include hybridizing at least one DNase fragmented parental nucleic acid with at least one additional DNase fragmented parental nucleic acid to provide the at least one hybridized nucleic acid.

In a third aspect, the present invention provides a method of recombining homologous or non-homologous nucleic acid sequences having low sequence similarity. The method includes recombining at least one set of fragmented nucleic acids with a set of cross-over codon-varied oligonucleotides, which oligonucleotides individually comprise a plurality of sequence diversity domains corresponding to a plurality of sequence diversity domains from homologous or non-homologous nucleic acids with low sequence similarity to produce a recombinant nucleic acid. The resulting recombinant nucleic acid is optionally selected for at least one desired trait or property.

This method of recombining sequences having low sequence similarity optionally includes fragmenting at least one of the homologous or non-homologous nucleic acids to provide the set of fragmented nucleic acids. The homologous or non-homologous nucleic acids are optionally fragmented with a DNase enzyme. The set of fragmented nucleic acids is also optionally provided by synthesizing a plurality of oligonucleotide fragments corresponding to at least one homologous or non-homologous nucleic acid.

A fourth aspect of this invention is a method of recombining a plurality of parental nucleic acids. This method includes ligating a set of a plurality of codon-varied oligonucleotides with a set comprising a plurality of nucleic acid sequences corresponding to a plurality of the parental nucleic acids to produce at least one recombinant nucleic acid encoding a full-length protein. The set includes at least a first oligonucleotide that is complementary to at least a first of the parental nucleic acids at a first region of sequence diversity and at least a second oligonucleotide which is complementary to at least a second of the parental nucleic acids at a second region of diversity.

Other features of this method include optionally ligating the set of a plurality of oligonucleotides with a ligase. The set of a plurality of oligonucleotides is optionally hybridized to a first parental nucleic acid and ligated with a ligase. Also, the plurality of parental nucleic acids is optionally homologous. Furthermore, the set of a plurality of oligonucleotides optionally comprises a set of overlapping codon-varied oligonucleotides. Finally, the method optionally includes hybridizing the set of a plurality of codon-varied oligonucleotides to at least one of the plurality of parental nucleic acids, elongating the oligonucleotides with a polymerase and ligating the resulting elongated oligonucleotides to produce a nucleic acid encoding a substantially full-length protein.

A fifth aspect of the invention relates to various compositions relevant to the methods described, supra, such as libraries produced by the methods, shuffling mixture compositions, and the like.

A sixth aspect of the present invention is an integrated system that optionally includes a computer or computer readable medium and character strings in a data set that represent a set of overlapping codon-varied oligonucleotides. This system optionally integrates a standard automatic synthesizer that is coupled to an output of the computer or computer readable medium. The automatic synthesizer accepts instructions from the computer or computer readable medium and those instructions, in turn, direct the synthesis of a desired set of codon-varied oligonucleotides. Additionally, the automated synthesizer system optionally integrates one or more robotic control elements for, e.g., incubating, denaturing, hybridizing, and elongating the set of oligonucleotides. This version of the integrated system optionally further includes a detector for, e.g., detecting an elongated nucleic acid.

Definitions

Unless otherwise indicated, the following definitions supplement those in the art.

A set of "codon-varied oligonucleotides" is a set of oligonucleotides, similar in sequence but with one or more base variations, where the variations corresponds to at least one encoded amino acid difference. The oligonucleotides are synthesized utilizing trinucleotide, i.e., codon-based coupling chemistry. Codon-varied oligonucleotide sequences can be based upon sequences of a selected set of homologous nucleic acids, where the oligonucleotide sequences can include regions of sequence identity and regions of sequence diversity with one or more of those homologous nucleic acids. Aside from being based upon homologous nucleic acid sequences, codon-varied oligonucleotide sequences can also be derived from non-homologous nucleic acids, or a combination of homologous and non-homologous sequences. "Sets" include a plurality of different members, e.g., 2, 3, 4, 5, 10, 20, 50, 100, 1,000 or more different members.

A "consensus region" sequence or subsequence is a region of a polynucleotide having a generalized sequence in which each nucleotide position represents the base most often found in actual sequence comparisons between homologous nucleic acids.

Two nucleic acids "correspond" when they have identical or complementary sequences, when one nucleic acid is a subsequence of the other, or when one sequence is derived naturally or artificially from the other.

A "cross-over" codon-varied oligonucleotide has regions of sequence identity with at least two members of a selected set of nucleic acids that are either homologous or non-homologous.

A "DNase enzyme" is an enzyme that catalyzes the cleavage of DNA, in vitro or in vivo. Many varieties of DNase enzymes are well characterized, e.g., in Berger and Kimmel, *Guide to Molecular Cloning Techniques, Methods in Enzymology* volume 152 Academic Press, Inc., San Diego, Calif.; Sambrook et al., *Molecular Cloning—A Laboratory Manual* (2nd Ed.), Vol. 1–3, Cold Spring Harbor Laboratory, Cold Spring Harbor, N.Y., 1989 and *Current Protocols in Molecular Biology*, F. M. Ausubel et al., eds., Current Protocols, a joint venture between Greene Publishing Associates, Inc. and John Wiley & Sons, Inc., (supplemented through 1998), and many are commercially available.

Nucleic acids are "elongated" in a reaction that incorporates additional nucleotides, or analogs thereof, into the nucleic acid sequence. The reaction is typically catalyzed by a polymerase, e.g., a DNA polymerase.

A set of "fragmented" nucleic acids results from the cleavage of at least one parental nucleic acid, e.g., enzymatically or chemically, or by providing subsequences of parental sequences in any other manner, including partially elongating a complimentary sequence with a polymerase or utilizing any synthetic format.

A "full-length protein" is a protein with substantially the same sequence domains as a corresponding protein encoded by a natural gene. Such a protein can have altered sequences relative to the corresponding naturally encoded gene, e.g., due to recombination and selection, but unless specified to the contrary, is typically at least about 95% the length of the naturally encoded gene.

Two nucleotide regions have high "sequence similarity" when one region is 90% or more identical to a second selected region when aligned for optimal correspondence. In contrast, regions of low "sequence similarity" refers to those regions that are at most 60% identical, more preferably, 40% or less identical, when aligned for maximal correspondence. Alignment may be accomplished manually or using a common alignment algorithm, such as, e.g., BLAST (set to default parameters).

Nucleic acids are "homologous" when they share sequence similarity that is derived, naturally or artificially, from a common ancestral sequence. This occurs naturally as two or more descendent sequences deviate from a common ancestral sequence over time as the result of mutation and natural selection. Artificially homologous sequences may be generated in various ways. For example, a nucleic acid sequence can be synthesized de novo to yield a nucleic acid that differs in sequence from a selected parental nucleic acid sequence. Artificial homology can also be created by artificially recombining one nucleic acid sequence with another, as occurs, e.g., during cloning or chemical mutagenesis, to produce a homologous descendent nucleic acid.

It is generally assumed that the two nucleic acids have common ancestry when they demonstrate sequence similarity. However, the exact level of sequence similarity necessary to establish homology varies in the art. In general, for purposes of this disclosure, two nucleic acid sequences are deemed to be homologous when they share enough sequence identity to permit direct recombination to occur between the two sequences.

It should be noted, however, that a specific advantage of this invention is the capacity to recombine nucleic acids that are more distantly related than other methods of recombination permit. In this aspect of the invention, nucleic acid sequences that are only distantly related, or not even detectably related, can be recombined by means of cross-over codon-varied oligonucleotides which are described, supra.

Nucleic acids "hybridize" when complementary single strands of nucleic acid pair to give a double-stranded nucleic acid sequence. Hybridization occurs due to a variety of well-characterized forces, including hydrogen bonding, solvent exclusion, and base stacking. An extensive guide to nucleic hybridization may be found in Tijssen (1993) *Laboratory Techniques in Biochemistry and Molecular Biology—Hybridization with Nucleic Acid Probes*, part I, chapter 2, "Overview of principles of hybridization and the strategy of nucleic acid probe assays," Elsevier, N.Y."

A "library" is a set of oligonucleotides. The set can be pooled, or can be individually accessible. The oligonucleotides may comprise DNA, RNA or combinations thereof.

Nucleic acid sequences are "overlapping" when they possess at least one complementary subsequence.

Nucleic acids are "non-homologous" when they lack shared sequence similarity with a common ancestral sequence, or when they can only be indirectly recombined utilizing oligonucleotide intermediates.

A nucleic acid "domain" is a discrete nucleic acid region or subsequence. It may be conserved or not conserved between a plurality of homologous nucleic acids. Generally, a domain is specified by comparing two or more sequences, where regions of sequence diversity between sequences constitutes a "sequence diversity domain," while a region of similarity is a "sequence similarity domain."

Two nucleic acids "recombine" when sequences from each of the two nucleic acids are combined in a progeny nucleic acid. Two sequences are "directly" recombined when both are substrates for recombination. Two sequences are "indirectly" recombined when the sequences are recombined by means of an intermediate such as a cross-over codon-varied oligonucleotide. When two nucleic acid sequences indirectly recombine, no more than one of those sequences is an actual substrate for recombination, and in some cases, neither sequence is a substrate for recombination.

A "substrate sequence" is at least one nucleotide covalently attached at its 3' end to a solid support.

The term "trinucleotide phosphoramidite sequence" is any codon sequence of nucleotides synthesized using standard phosporamidite chemistry. Many sources have described such synthesis, e.g., Virnekäs, B. et al., (1994) *Nucleic Acids Res.*, 22, 5600–5607 and Kayushin, A. L. et al., (1996) *Nucleic Acids Res.*, 24, 3748–3755.

Figure 1:
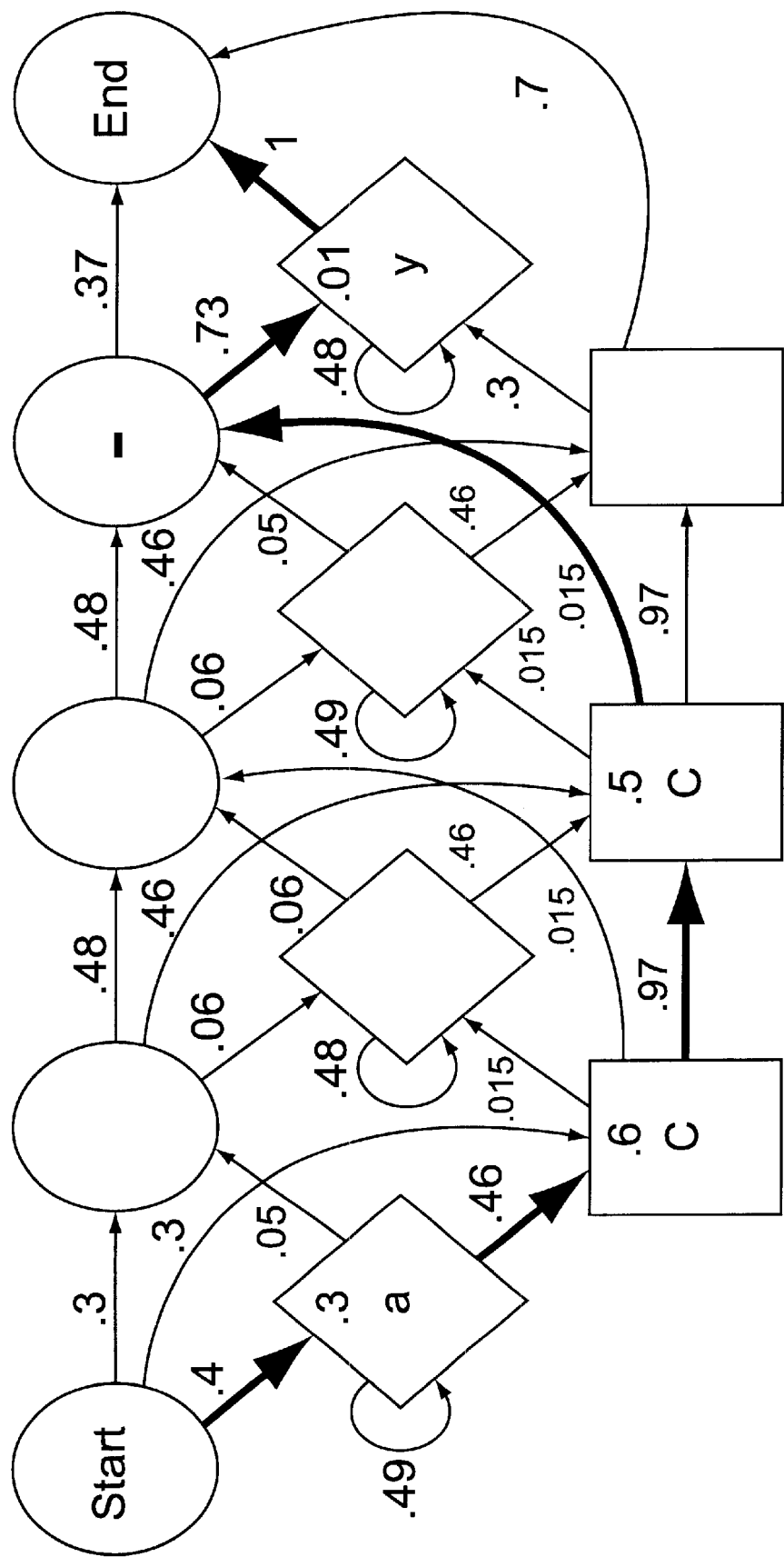
FIG. 1 is a possible hidden Markov model for the protein ACCY.

DETAILED DISCUSSION OF THE INVENTION
Introduction

The present invention provides recombination methodologies in which codon-varied oligonucleotides are used to provide recombined nucleic acid populations. Codon-varied oligonucleotides are chemically synthesized utilizing trinucleotide phosphoramidite sequences. These oligonucleotides can be derived from homologous or non-homologous nucleic acid sequences, or combinations of such sequences. In general, the use of codon-varied oligonucleotides as libraries for recombination and/or gene synthesis significantly enhances the rate of shuffling processes. Furthermore, codon-varied oligonucleotide intermediates may be used to achieve indirect recombination of nucleic acid sequences that would not otherwise recombine.

Mononucleotide-based oligonucleotide synthesis has significant limitations compared to trinucleotide-based formats. One major limitation presented by mononucleotide formats, when adding diversity, stems from the degeneracy of the genetic code. For example, if serine (via UCC only) or glycine (via GGC only) (preferred codon in parentheses) is desired at a specific position, mononucleotide-based synthesis leads to a degenerate oligonucleotide encoding KSS. However, the KSS oligonucleotide also leads to the insertion of undesired amino acids, e.g., as follows: tryptophan (UGG), cysteine (UGC), and alanine (GCC). In contrast, a trinucleotide-generated codon-varied oligonucleotide would result solely in the preferred insertions.

Prior to the present invention, trinucleotide phosphoramidites had not been used to synthesize codon-varied oligonucleotides for use in DNA shuffling. Advantages of this method include being able to shuffle DNA at various levels, e.g., as defined polynucleotide fragments or as individual codon sequences. Amino acids at any position can be designated specifically, incorporated in a biased manner, or inserted randomly. Additionally, being codon-based, any deletions and insertions, whether intended or due to error, that may occur during synthesis, will not offset the coding frame of reference and in turn, will be less likely to inactivate encoded shuffled proteins. As such, the present invention will enhance the capacity of DNA shuffling as an artificial evolution technique.

In overview, the present invention initially entails determining the specific nucleic acid sequences that are to be synthesized as codon-varied oligonucleotides and in turn, which form compositions for recombination. Nucleic acid synthesis, as well as other aspects of the invention, can be conducted in a fully integrated system that incorporates a computer coupled to an automatic synthesizer and one or more robotic control elements. Oligonucleotides can be synthesized using either a trinucleotide coupling format or by mononucleotide synthesis in a split-pool format. Following synthesis, recombination can be carried out using one of several alternative methods. Finally, desired traits or properties can be selected using techniques that are known in the art.

The following provides details regarding the various aspects of the recombination methods of the present invention, including synthesis, hybridization, elongation, and selection protocols. It also provides details regarding the different compositions and integrated systems of the present invention.

Selection of Homologous/Non-Homologous Nuceic Acid Sequences to be Synthesized as Codon-Varied Oligonucleotides for Recombination A threshold issue in practicing the present invention is selecting or designing the sequences of the codon-varied oligonucleotides to be synthesized. They can be derived from nucleic acid sequences that are homologous, non-homologous, and/or purely practitioner designed. In an aspect of the invention, designated mixtures of trinucleotide phosphoramidites can be used to vary an amino acid at any position according to practitioner specifications. Additionally, positions may be made either random or biased by any pattern, and for family shuffling each amino acid position can be varied with respect to known natural or artificial diversity. Also, deletions and insertions can be programmed or the reaction conditions can be adjusted so that they occur at some frequency. In another aspect, multiple natural and/or designed parent sequences having defined motifs can be synthesized. According to this method, it is useful to create hybrid parents that together contain the sequence elements of the parents, but which are "pre-shuffled" so as to promote shuffling with the natural parents.

Sequence information available from nucleic acid databases are useful references during the selection and design process. Genbank®, Entrez®, EMBL, DDBJ, and the NCBI are examples of public database/search services that can be accessed. Many sequence databases are available via the internet or on a contract basis from a variety of companies specializing in genomic information generation and/or storage. When shuffling homologous nucleic acids, the present invention optionally includes aligning homologous nucleic acid sequences or regions of similarity. For example, in one aspect, the invention relates to a method of recombining at least two parental nucleic acids. In an embodiment of this method, the composition of nucleic acids to be recombined is provided by aligning homologous nucleic acid sequences to select conserved regions of sequence identity and regions of sequence diversity. Codon-varied oligonucleotides are then synthesized to correspond to at least one region of sequence diversity. Similarly, an aspect of the invention includes deriving the sequences of a second set of overlapping codon-varied oligonucleotides from first round selected nucleic acids by aligning those first round sequences to identify regions of identity and regions of diversity.

In these processes of sequence comparison and homology determination, one sequence is often used as a reference against which other test nucleic acid sequences are compared. This comparison can be accomplished with the aid of a sequence comparison algorithm, i.e., instruction set, or by visual inspection. When an algorithm is employed, test and reference sequences are input into a computer, subsequence coordinates are designated, as necessary, and sequence algorithm program parameters are specified. The algorithm then calculates the percent sequence identity for the test nucleic acid sequence(s) relative to the reference sequence, based on the specified program parameters.

For purposes of the present invention, suitable sequence comparisons can be executed, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., supra).

One example of an algorithm that can be used to determine percent sequence identity and sequence similarity is the BLAST algorithm, which is described, e.g., in Altschul et al., *J. Mol. Biol.* 215:403–410 (1990). Software for performing BLAST analyses is publicly available through the National Center for Biotechnology Information (http://www.ncbi.nlm.nih.gov/).

An example of aligning proteins of unknown function relies on the flexible statistical model called the hidden Markov model (HMM). This model utilizes defined 'threading' through a multiple sequence alignment. The threading matrix, but not the sequence alignment consensus itself, is subsequently used to identify novel proteins that can be clustered with the original group of HMM structures. HMM or variations thereof can be excellent statistical tools used in defining sequences and divergence in split-pool synthesis of codon-varied oligonucleotides. Using the HMM matrix, each position is given a certain set of options (e.g., delete, insert or add the next amino acid) and the percentage of codon-varied oligonucleotide-carrying beads going down each path can easily be calculated based on a parental display.

As shown in FIG. 1, the typical profile hidden Markov model is a chain of match (square), insert (diamond), and delete (circle) nodes, with all transitions between nodes and all character costs in the insert and match nodes trained to specific probabilities (i.e., the known parents). The single best path through an HMM corresponds to a path from a start state to an end state in which each character of the sequence is related to a successive match or insertion state along that path. Delete states indicate that the sequence has no character corresponding to that position in the HMM.

Transitions from state to state progress from left to right through the model, with the exception of self-loops on insertion states (FIG. 1). The self-loops allow deletions of any length to fit the model, regardless of the length of other sequences in the family.

A path through the model can represent any sequence. The probability of any sequence, given the model, is computed by multiplying the emission and transition probabilities along the path. FIG. 1 illustrates a possible hidden Markov model for the peptide ACCY. As shown, a path through the model represented by ACCY is highlighted. The peptide is represented as a sequence of probabilities. The numbers in the boxes show the probability that an amino acid occurs in a particular state, and the number next to the directed arcs show probabilities which connect the states. For instance, the probability of A being emitted in position one is 0.3, and the probability of C being emitted in position two is 0.6. The probability of ACCY along this path is:

$$0.4*0.3*0.46*0.6*0.97*0.5*0.015*0.73*0.01*1=1.76\times10^{-6}.$$

Or, by transforming probabilities to logs so that addition can replace multiplication:

$$\log_e(0.4)+\log_e(0.3)+\log_e(0.46)+\log_e(0.6)+\log_e(0.97)+\log_e(0.5)+\log_e(0.015)+\log_e(0.73)+\log_e(0.01)+\log_e(1)=-13.25.$$

Codon-Varied Oligonucleotide Synthesis

One aspect of the present invention comprises synthesizing codon-varied oligonucleotides which are then used to achieve recombination. Codon-varied oligonucleotides can be synthesized utilizing trinucleotide-based phosphoramidite coupling chemistry, in which trinucleotide phosphoramidites representing codons for all amino acids are used to introduce entire codons into oligonucleotide sequences synthesized by this solid-phase technique. An advantage of this trinucleotide synthetic approach is that it provides tremendous flexibility to shuffling processes as codon-varied oligonucleotide sequences can be selected or designed by the practitioner, e.g., to be based upon homologous or non-homologous nucleotide sequences, or combinations of such sequences.

The synthesis of trinucleotide phoshoramidites, their subsequent use in oligonucleotide synthesis, and related issues are described in, e.g., Virnekäs, B., et al., (1994) *Nucleic Acids Res.*, 22, 5600–5607, Kayushin, A. L. et al., (1996) *Nucleic Acids Res.*, 24, 3748–3755, Huse, U.S. Pat. No. 5,264,563 "PROCESS FOR SYNTHESIZING OLIGONUCLEOTIDES WITH RANDOM CODONS," Lyttle et al., U.S. Pat. No. 5,717,085 "PROCESS FOR PREPARING CODON AMIDITIES," Shortle et al., U.S. Pat. No. 5,869,644 "SYNTHESIS OF DIVERSE AND USEFUL COLLECTIONS OF OLIGONUCLEOTIDES," Greyson, U.S. Pat. No. 5,789,577 "METHOD FOR THE CONTROLLED SYNTHESIS OF POLYNUCLEOTIDE MIXTURES WHICH ENCODE DESIRED MIXTURES OF PEPTIDES," and Huse, WO 92/06176 "SURFACE EXPRESSION LIBRARIES OF RANDOMIZED PEPTIDES."

In the present invention, codon-varied oligonucleotides can be synthesized using various trinucleotide-related techniques, e.g., the trinucleotide synthesis format and/or the split-pool synthesis format. The individual steps for performing both formats are described, infra. Preferably, all of the oligonucleotides of a selected length (e.g., about 20, 30, 40, 50, 60, 70, 80, 90, or 100 or more nucleotides) which incorporate the chosen nucleic acid sequences are synthesized.

In general, overlapping codon-varied oligonucleotides, synthesized according to the methods of the present invention, can have, e.g., about 10 bases of sequence identity to either side of a region of variance to ensure reasonably efficient recombination. However, flanking regions with identical bases can have fewer identical bases (e.g., 5, 6, 7, 8, or 9) and can, of course, have larger regions of identity (e.g., 11, 12, 13, 14, 15, 16, 17, 18, ,19, 20, 25, 30, 50, or more.

The trinucleotide synthesis format includes providing a substrate sequence having a 5' terminus and at least one base, both of which have protecting groups thereon. The 5' protecting group of the substrate sequence is then removed to provide a 5' deprotected substrate sequence, which is then coupled with a selected trinucleotide phosphoramidite sequence. The trinucleotide has a 3' terminus, a 5' terminus, and three bases, each of which has protecting groups thereon. The coupling step yields an extended oligonucleotide sequence. Thereafter, the removing and coupling steps are optionally repeated. When these steps are repeated, the extended oligonucleotide sequence yielded by each repeated coupling step becomes the substrate sequence of the next repeated removing step until a desired codon-varied oligonucleotide is obtained. This basic synthesis format can optionally include coupling together one or more of: mononucleotides, trinucleotide phosphoramidite sequences, and oligonucleotides.

The split-pool synthesis format includes providing substrate sequences, each having a 5' terminus and at least one base, both of which have protecting groups thereon. The 5' protecting groups of the substrate sequences are removed to provide 5' deprotected substrate sequences, which are then coupled with selected trinucleotide phosphoramidite sequences. Each trinucleotide has a 3' terminus, a 5' terminus, and three bases, all of which have protecting groups thereon. The coupling step yields extended oligonucleotide sequences. Thereafter, the removing and coupling steps are optionally repeated. When these steps are repeated, the extended oligonucleotide sequences yielded by each repeated coupling step become the substrate sequences of the next repeated removing step until extended intermediate oligonucleotide sequences are produced.

Additional steps of the split-pool format optionally include splitting the extended intermediate oligonucleotide sequences into two or more separate pools. After this is done, the 5' protecting groups of the extended intermediate oligonucleotide sequences are removed to provide 5' deprotected extended intermediate oligonucleotide sequences in the two or more separate pools. Following this, these 5' deprotected intermediates are coupled with one or more selected mononucleotides, trinucleotide phosphoramidite sequences, or oligonucleotides in the two or more separate pools to yield further extended intermediate oligonucleotide sequences. In turn, these further extended sequences are pooled into a single pool. Thereafter, the steps beginning with the removal of the 5' protecting groups of the substrate sequences to provide 5' deprotected substrate sequences are optionally repeated. When these steps are repeated, the further extended oligonucleotide sequences, yielded by each repeated coupling step that generates those specific sequences, become the substrate sequences of the next repeated removing step that includes those specific sequences until desired codon-varied oligonucleotides are obtained.

The split-pool synthesis format is particularly advantageous when sequences having low homology (e.g., <90%) are to be synthesized. For example, it enables the practitioner to precisely control the way sequences being elongated are dispersed within a framework of defined nucleic acid sequences. Utilizing this format, one can now take co-variance among divergent parental nucleic acids into account by being able to define the exact point where recombination is to occur and what percentage of those parents will form a chimera at that point. Further, co-evolution and systematic variation within a nucleic acid sequence can be captured using this module-based format.

In this approach, the smallest module within each genetic sequence is the codon, i.e., a single trinucleotide in length, while larger modules are, e.g., at least 15–90 or more nucleotides in length, which can be a structurally defined segment, or a sequence of less or no homology to related parent nucleic acids. Also, one can foresee the use of a random or Poisson distribution of sequence sizes to initiate the shuffling process. This would mimic current recombination methods, but in a synthetic and controlled format.

The chemistry involved in both the trinucleotide and the split-pool codon-varied oligonucleotide synthetic methods is known to those of skill. In general, both methods utilize phosphoramidite solid-phase chemical synthesis in which the 3' ends of nucleic acid substrate sequences are covalently attached to a solid support, e.g., controlled pore glass. The 5' protecting groups can be, e.g., a triphenylmethyl group, such as, dimethoxyltrityl (DMT) or monomethyoxytrityl, a carbonyl-containing group, such as, 9-fluorenylmethyloxycarbonyl (FMOC) or levulinoyl, an acid-clearable group, such as, pixyl, a fluoride-cleavable alkylsilyl group, such as, tert-butyl dimethylsilyl (T-B-DMSi), triisopropyl silyl, or trimethylsilyl. The 3' protecting groups can be, e.g., β-cyanoethyl groups.

Both synthesis formats can optionally be performed in an integrated automated synthesizer system that automatically performs the synthetic steps. This aspect includes inputting character string information into a computer, the output of which then directs the automated synthesizer to perform the steps necessary to synthesize the desired codon-varied oligonucleotides. This integrated system is discussed further, infra.

To further ensure that functional, full-length shuffled genes are ultimately obtained certain techniques can be utilized following codon-varied oligonucleotide synthesis. For example, gel purification is one method that can be used to purify synthesized oligonucleotides. High-performance liquid chromatography can be similarly employed.

Following synthesis, translational coupling can be used to assess gene functionality, e.g., to test whether full-length sequences are generated. In this process, the translation of a reporter protein, e.g., green fluorescent protein or β-galactosidase is coupled to that of the shuffled gene product. This enables one to distinguish full-length shuffled genes from those that contain deletions or frame shifts. The subsequent selection of desired traits or properties of the shuffled gene is discussed further, infra.

The various references already discussed which relate to oligonucleotide synthesis provide further details on synthesis of oligonucleotides by either trinucleotide or mononucleotide chemical synthesis.

Recombination Methods of the Present Invention

The present invention provides several methods for shuffling nucleic acid sequences. In one aspect, the invention is directed to a method of recombining codon-varied oligonucleotides to provide a population of recombined nucleic acids. Following oligonucleotide synthesis, this method comprises hybridizing and elongating a set of overlapping codon-varied oligonucleotides to provide the population of recombined nucleic acids. The invention also provides a method of recombining at least two parental nucleic acids to provide at least one recombinant nucleic acid. Beyond providing a composition comprising at least one set of fragmented parental nucleic acids, the composition is similarly hybridized and the hybridization product is then elongated to provide recombinant nucleic acids that comprise at least one subsequence from each of the two parental nucleic acids. Another method of the invention is that of recombining homologous or non-homologous nucleic acid sequences having low sequence similarity. This method comprises, e.g., recombining at least one set of fragmented nucleic acids with a set of cross-over codon-varied oligonucleotides. This recombination method also involves hybridization and elongation steps.

In Vitro Recombination

According to certain methods of the invention, overlapping codon-varied oligonucleotides can be recombined in vitro, e.g., in a pool of such sequences. For example, a set of single-stranded codon-varied oligonucleotides can be synthesized, with individual members having sequences that are complementary to one another. Such single-stranded sequences can then be hybridized, e.g., by cooling to 20° C. to 75° C., and preferably from 40° C. to 65° C. Hybridization can be accelerated by the addition of polyethylene glycol ("PEG") or salt. The salt concentration is preferably from 0 mM to 600 mM, more preferably the salt concentration is from 10 mM to 100 mM. The salt can be such salts as $(NH_4)_2SO_4$, KCl, or NaCl. The concentration of PEG is preferably from 0% to 20%, more preferably from 5% to 10%.

During elongation, the hybridized codon-varied oligonucleotides are then incubated in the presence of a nucleic acid polymerase, e.g., Taq or Klenow, and dNTP's (i.e., dATP, dCTP, dGTP and dTTP). If regions of sequence identity are large, Taq or other high-temperature polymerase can be used with a hybridization temperature of between 45°–65° C. If the areas of identity are small, Klenow or other low-temperature polymerases can be used with a hybridization temperature of between 20°–30° C. The polymerase can be added to the random nucleic acid fragments prior to, simultaneously with, or after hybridization. As noted elsewhere in this disclosure, certain embodiments of the invention can involve denaturing the resulting elongated double-stranded nucleic acid sequences and then hybridizing and elongating those sequences again. This cycle can be repeated for any desired number of times. Preferably the cycle is repeated from 2 to 100 times, more preferably the sequence is repeated from 10 to 40 times.

In Vivo Recombination

An embodiment of the present invention involves in vivo recombination. In this embodiment, a population of codon-varied oligonucleotides can be introduced into bacterial or eukaryotic cells under conditions such that at least one codon-varied oligonucleotide sequence is present in each host cell. Oligonucleotide sequences can be introduced into host cells using various methods known in the art, e.g., calcium chloride treatment, electroporation, transfection, lipofection, biolistics, conjugation, and the like. In vivo recombination formats that can optionally be used in the present invention are, e.g., plasmid-plasmid recombination, virus-plasmid recombination, virus-virus recombination, chromosome recombination, virus-chromosome recombination, chimeric recombination in which the codon-varied oligonucleotides are chimeraplasts, and the like. For example, when two oligonucleotide sequences that have regions of identity are inserted into the host cells homologous recombination occurs between the two sequences.

After transformation, the host cell transformants are placed under selection to identify those host cell transformants which contain specific nucleic acid sequences having desired traits or properties. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the shuffled population which shows enhanced binding to the ligand. Alternatively, the protein can be expressed in another system to ensure proper processing. The steps of this process can be repeated for multiple cycles.

The host cells can also be recursively recombined via, e.g., protoplast fusion and other whole genome shuffling methodologies to increase the diversity of the cell populations. Whole genome shuffling methods are described in detail in International Application Nos. PCT/US98/00852 and PCT/US99/15972, filed Jan. 16, 1998 and Jul. 15, 1999, respectively.

Recombination by Ligation

One aspect of the present invention relates to a method of performing recombination between nucleic acids by ligation of libraries of codon-varied oligonucleotides corresponding to the nucleic acids to be recombined. In this format, a set of a plurality of codon-varied oligonucleotides which includes a plurality of nucleic acid sequences from a plurality of the parental nucleic acids are ligated to produce a recombinant nucleic acid, typically encoding a full length protein (although ligation can also be used to make libraries of partial nucleic acid sequences which can then be recombined, e.g., to produce a partial or full-length recombinant nucleic acid via ligation or polymerase-mediated methods). The oligonucleotide set typically includes at least a first oligonucleotide which is complementary to at least a first of the parental nucleic acids at a first region of sequence diversity and at least a second oligonucleotide which is complementary to at least a second of the parental nucleic acids at a second region of diversity. The parental nucleic acids can be homologous or non-homologous.

Typically, the codon-varied oligonucleotides are ligated with a ligase. In one general format, the oligonucleotides are hybridized to a first parental nucleic acid which acts as a template, and ligated with a ligase. The codon-varied oligonucleotides may be extended with a polymerase and ligated. The polymerase can be, e.g., an ordinary DNA polymerase or a thermostable DNA polymerase. The ligase can also be, e.g., an ordinary DNA ligase or a thermostable DNA ligase. Many such polymerases and ligases are commercially available.

In one set of approaches to recombination, a common element is the preparation of a single-stranded (ss) template to which codon-varied oligonucleotide primers are annealed and then elongated by a DNA polymerase in the presence of dNTP's and an appropriate buffer. The gapped duplex can be sealed with ligase prior to, e.g., transformation or electroporation into *E. coli*, where the newly synthesized strand is replicated and generates a chimeric gene with contributions from the codon-varied oligonucleotide in the context of the single-stranded (ss) parent.

The ss template to which codon-varied oligonucleotides can be annealed can be prepared, for example, by the incorporation of the phage IG region into a plasmid and use of a helper phage such as M13KO7 (Pharmacia Biotech) or R408 to package ss plasmids into filamentous phage particles. Optionally, the ss template can be generated by denaturation of a double-stranded (ds) template and annealing in the presence of the codon-varied oligonucleotide primers.

Enrichment methods vary for isolating newly synthesized chimeric strand over the parental template strand. Isolation and selection of ds templates can be performed using available methods. See e.g., Ling et al. (1997) "Approaches to DNA mutagenesis: an overview" *Anal Biochem.*, December 15;254(2):157–78; Dale et al. (1996) "Oligonucleotide-directed random mutagenesis using the phosphorothioate method" *Methods Mol Biol.*, 57:369–74; and Smith (1985) "In vitro mutagenesis" *Ann. Rev. Genet.*, 19:423–462.

In one aspect, for example, a "Kunkel style" method uses uracil containing templates. Similarly, the "Eckstein" method uses phosphorothioate-modified DNA (Taylor et al. (1985) "The use of phosphorothioate-modified DNA in restriction enzyme reactions to prepare nicked DNA." *Nucleic Acids Res.* 13:8749–8764; Taylor et al. (1985) "The rapid generation of oligonucleotide-directed mutations at high frequency using phosphorothioate-modified DNA" *Nucleic Acids Res.* 13:8765–8787; Nakamaye & Eckstein (1986) "Inhibition of restriction endonuclease Nci I cleavage by phosphorothioate groups and its application to oligonucleotide-directed mutagenesis." *Nucleic Acids Res.* 14:9679–9698; Sayers et al. (1988). "Y-T Exonucleases in phosphorothioate-based oligonucleotide-directed mutagenesis." *Nucleic Acids Res.* 16:791–802; Sayers et al. (1988) "5'-3' Strand specific cleavage of phosphorothioate-containing DNA by reaction with restriction endonucleases in the presence of ethidium bromide" *Nucleic Acids Res.* 16:803–814). The use of restriction selection, or e.g., purification can be used in conjunction with mismatch repair deficient strains (see, e.g., Carter et al. (1985) "Improved oligonucleotide site directed mutagenesis using M13 vectors" *Nucleic Acids Res.* 13, 4431–4443 Carter (1987) "Improved oligonucleotide-directed mutagenesis using M13 vectors." *Methods in Enzymol.* 154:382–403; Wells (1986) "Importance of hydrogen bond formation in stabilizing the transition state of subtilisin." *Trans. R. Soc. Lond.* A317, 415–423).

The "mutagenic" primers used in these methods can be codon-varied oligonucleotide(s) encoding, e.g., any type of randomization, insertion, deletion based on sequence diversity of homologous genes, etc. Multiple codon-varied oligonucleotide primers can anneal to a given template and be extended to create multiply chimeric genes. The use of a DNA polymerase such as those from phages T4 or T7 are suitable for this purpose as they do not degrade or displace a downstream primer from the template.

In one example, DNA shuffling is performed using uracil containing templates. In this embodiment, the gene of interest is cloned into an *E. coli* plasmid containing the filamentous phage intergenic (IG, ori) region. Single stranded (ss) plasmid DNA is packaged into phage particles upon infection with a helper phage such as M13KO7 (Pharmacia) or R408 and can be easily purified by methods such as phenol/chloroform extraction and ethanol precipitation. If this DNA is prepared in a dut– ung– strain of *E. coli*, a small number of uracil residues are incorporated into it in place of the normal thymine residues. One or more codon-varied oligonucleotide primers are annealed to the ss uracil-containing template by heating to 90° C. and slowly cooling to room temperature. An appropriate buffer containing all 4 dNTPs, T7 DNA polymerase and T4 DNA ligase is added to the annealed template/primer mix and incubated between room temperature –37° C. for $\geq$1 hour. The T7 DNA polymerase extends from the 3' end of the codon-varied oligonucleotide primer and synthesizes a complementary strand to the template incorporating the primer. DNA ligase seals the gap between the 3' end of the newly synthesized strand and the 5' end of the primer. If multiple codon-varied oligonucleotide primers are used, then the polymerase will extend to the next primer, stop and ligase will seal the gap. This reaction is then transformed into an ung+ strain of *E. coli* and antibiotic selection for the plasmid is applied. The uracil N-glycosylase (ung gene product) enzyme in the host cell will recognize the uracil in the template strand and removes it, creating apyrimidinic sites that are either not replicated or the host repair systems will correct it by using the newly synthesized strand as a template. The resulting plasmids predominantly contain the desired change in the gene if interest. If multiple codon-varied oligonucleotide primers are used then it is possible to simultaneously introduce numerous changes in a single reaction. If the codon-varied oligonucleotide primers are derived from or correspond to fragments of homologous genes, then multiply chimeric genes can be generated.

Iterative Codon-Varied Oligonucleotide-Mediated Recombination Methods

In one embodiment, the present invention provides iterative codon-varied oligonucleotide-mediated recombination formats. These formats can be combined with standard recombination methods, also, optionally, in an iterative format.

In particular, recombinant nucleic acids produced by codon-varied oligonucleotide-mediated recombination can be screened for activity and sequenced. The sequenced recombinant nucleic acids are aligned and regions of identity and diversity are identified. Codon-varied oligonucleotides are then selected for recombination of the sequenced recombinant nucleic acids. This process of screening, sequencing active recombinant nucleic acids and recombining the active recombinant nucleic acids can be iteratively repeated until a molecule with a desired trait or property is obtained.

In addition, recombinant nucleic acids made using codon-varied oligonucleotides can be cleaved and shuffled using standard recombination methods, which are, optionally, reiterative. Standard recombination can be used in conjunction with oligonucleotide shuffling and either or both steps are optionally reiteratively repeated.

An example of iterative shuffling by oligonucleotide mediated recombination of codon-varied oligonucleotides occurs when extremely fine grain shuffling is desired. For example, small genes encoding small protein such as defensins (antifungal proteins of about 50 amino acids), EF40 (an antifungal protein family of about 28 amino acids), peptide antibiotics, peptide insecticidal proteins, peptide hormones, many cytokines and many other small proteins, are difficult to recombine by standard recombination methods, because the recombination occurs with a frequency that is roughly the same as the size of the gene to be recombined, limiting the diversity resulting from recombination. In contrast, oligonucleotide-mediated recombination methods can recombine essentially any region of diversity in any set of sequences, with crossovers occurring at any selected base-pair.

Thus, libraries of sequences prepared by recursive codon-varied oligonucleotide mediated recombination are optionally screened and selected for a desired property, and improved (or otherwise desirable) clones are sequenced with the process being iteratively repeated to generate additional libraries of nucleic acids. Thus, additional recombination rounds are performed either by standard fragmentation-based recombination methods, or by sequencing positive clones, designing appropriate family shuffling oligonucleotides and performing a second round of recombination/selection to produce an additional library (which can be recombined as described). In addition, libraries made from different recombination rounds can also be recombined, either by sequencing and oligonucleotide recombination or by standard recombination methods.

Selection of a Desired Trait or Property

The exact nature of the selection or screening method that is used following the recombination procedures herein is not a critical aspect of the invention. One or more recombination cycle(s) is/are optionally followed by at least one cycle of selection for molecules having desired traits or properties. If a recombination cycle is performed in vitro, the products of recombination, i.e., recombinant nucleic acids, are sometimes introduced into cells before the selection step. Recombinant nucleic acids can also be linked to an appropriate vector or to other regulatory sequences before selection. Alternatively, products of recombination generated in vitro are sometimes packaged in viruses (e.g., bacteriophage) before selection. If recombination is performed in vivo, recombination products may sometimes be selected in the cells in which recombination occurred. In other applications, recombinant segments are extracted from the cells, and optionally packaged as viruses or other vectors, before selection.

The nature of selection depends on what trait or property is to be acquired or for which improvement is sought. It is not usually necessary to understand the molecular basis by which particular recombination products have acquired new or improved traits or properties relative to the starting substrates. For instance, a gene has many component sequences, each having a different intended role (e.g., coding sequences, regulatory sequences, targeting sequences, stability-conferring sequences, subunit sequences and sequences affecting integration). Each of these component sequences are optionally varied and recombined simultaneously. Selection is then performed, for example, for recombinant products that have an increased ability to confer activity upon a cell without the need to attribute such improvement to any of the individual component sequences of the vector.

Depending on the particular protocol used to select for a desired trait or property, initial round(s) of screening can sometimes be performed using bacterial cells due to high transfection efficiencies and ease of culture. However, yeast, fungal or other eukaryotic systems may also be used for library expression and screening when bacterial expression is not practical or desired. Similarly, other types of selection that are not amenable to screening in bacterial or simple eukaryotic library cells, are performed in cells selected for use in an environment close to that of their intended use. Final rounds of screening are optionally performed in the precise cell type of intended use.

When further improvement in a trait is sought, at least one and usually a collection of recombinant products surviving a first round of screening/selection are optionally subject to a further round of recombination. These recombinant products can be recombined with each other or with exogenous segments representing the original substrates or further variants thereof. Again, recombination can proceed in vitro or in vivo. If the previous screening step identifies desired recombinant products as components of cells, the components can be subjected to further recombination in vivo, or can be subjected to further recombination in vitro, or can be isolated before performing a round of in vitro recombination. Conversely, if the previous selection step identifies desired recombinant products in naked form or as components of viruses, these segments can be introduced into cells to perform a round of in vivo recombination. The second round of recombination, irrespective how performed, generates additionally recombined products which encompass more diversity than is present in recombinant products resulting from previous rounds.

The second round of recombination may be followed by still further rounds of screening/selection according to the principles discussed for the first round. The stringency of selection can be increased between rounds. Also, the nature of the screen and the trait or property being selected may be varied between rounds if improvement in more than one trait or property is sought. Additional rounds of recombination and screening can then be performed until the recombinant products have sufficiently evolved to acquire the desired new or improved trait or property.

Multiple cycles of recombination can be performed to increase library diversity before a round of selection is performed. Alternately, where the library is diverse, multiple rounds of selection can be performed prior to recombination methods.

General texts that describe molecular biological techniques useful herein, including mutagenesis, library construction, screening assays, cell culture and the like include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1–3, Cold Spring Harbor Laboratory, Cold Spring Harbor, N.Y., 1989 (Sambrook); and *Current Protocols in Molecular Biology*, F. M. Ausubel et al., eds., Current Protocols, a joint venture between Greene Publishing Associates, Inc. and John Wiley & Sons, Inc., (supplemented through 1998) (Ausubel). Methods of transducing cells, including plant and animal cells, with nucleic acids are generally available, as are methods of expressing proteins encoded by such nucleic acids. In addition to Berger, Ausubel and Sambrook, useful general references for culture of animal cells include Freshney (*Culture of Animal Cells, a Manual of Basic Technique*, third edition Wiley-Liss, New York (1994)) and the references cited therein, Humason (*Animal Tissue Techniques*, fourth edition W. H. Freeman and Company (1979)) and Ricciardelli, et al., *In Vitro Cell Dev. Biol.* 25:1016–1024 (1989). References for plant cell cloning, culture and regeneration include Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York)(Gamborg). A variety of Cell culture media are described in Atlas and Parks (eds) *The Handbook of Microbiological Media* (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS).

Composition of Populations to be Recombined

The present invention provides for the recombination of codon-varied oligonucleotides that are derived from homologous or non-homologous nucleic acid sequences, or combinations of such sequences. As such, the conceivable compositions of populations to be recombined applicable to the present invention are infinite, and specific codon-varied oligonucleotide sequences to be recombined can be presented in biased or unbiased concentrations in the composition. Particular compositions that are relevant to the invention are discussed, infra.

The composition of the method of recombining at least two parental nucleic acids can be provided by initially aligning homologous nucleic acid sequences to select conserved regions of sequence identity and regions of sequence diversity. Optionally, this initial step can include selecting non-homologous nucleic acids to be recombined. The next step, in the case of homologous sequence selection, includes synthesizing a plurality of overlapping codon-varied oligonucleotides corresponding to at least one region of sequence diversity. On the other hand, if non-homologous sequences are selected, the next step includes synthesizing a plurality of overlapping codon-varied oligonucleotides that correspond to at least one subsequence from each of the at least two parental nucleic acids. Then, irrespective of the sequence-type initially selected, at least one full-length nucleic acid that is identical to, or homologous with, at least one of the homologous, i.e., parental nucleic acid sequences is provided and fragmented by DNase cleavage. Finally, the resulting set of nucleic acid fragments is mixed with the plurality of overlapping codon-varied oligonucleotides to provide the composition comprising at least one set of fragmented parental nucleic acids corresponding to the at least two parental nucleic acids with the set of fragmented parental nucleic acids including a plurality of overlapping codon-varied oligonucleotides.

An additional aspect of the present invention is a composition including a library of codon-varied oligonucleotides that comprises a plurality of codon-varied oligonucleotide member types which correspond to a plurality of subsequence regions of a plurality of members of a selected set of a plurality of homologous or non-homologous target sequences, which member types comprise a plurality of members with at least one region of similarity and at least one region of diversity. The region of diversity includes at least one codon difference. Also, the plurality of oligonucleotide member types of this composition can be present in non-equimolar amounts.

The composition described above can include a plurality of subsequence regions that include a plurality of non-overlapping sequence regions of the selected set of a plurality of homologous target sequences. This composition can, alternatively, include a plurality of oligonucleotide member types, each having a sequence identical to at least one subsequence from at least one of the selected set of target sequences in which those target sequences are identical. The composition can also be a plurality of oligonucleotide member types comprising a plurality of homologous oligonucleotides corresponding to a homologous region from the selected set of a plurality of homologous target sequences, where each of the plurality of homologous oligonucleotides comprise at least one codon-varied subsequence.

The shuffling compositions of the invention can include at least one of: a polymerase, a thermostable DNA polymerase, a nucleic acid synthesis reagent, a buffer, a salt, magnesium, and at least one nucleic acid sequence comprising at least one of the plurality of members of the selected set of homologous target sequences. This composition can also include a plurality of oligonucleotide member types that is selected by aligning a plurality of homologous or non-homologous target sequences, determining at least one region of identity and at least one region of diversity and synthesizing the oligonucleotides to encode at least a portion of the at least one region of identity, or at least a portion of the at least one region of diversity, or at least a portion of both.

Additionally, the compositions can include a plurality of oligonucleotide member types comprising at least one member type comprising at least one sequence diversity domain, or a plurality of sequence diversity domains. In the case when the composition is a plurality of oligonucleotide member types comprising at least one member type comprising a plurality of sequence diversity domains, the plurality of sequence diversity domains can correspond to adjacent sequence regions on a plurality of the plurality of homologous nucleic acids when the homologous nucleic acids are aligned. Finally, the composition can be a library that comprises a set of cross-over codon-varied oligonucleotides with each oligonucleotide member of the set of cross-over codon-varied oligonucleotides including a plurality of sequence diversity domains corresponding to a plurality of homologous nucleic acids.

Utilization of Oligonucleotide-Mediated Blending to Tune Recombination

In certain embodiments of the invention, recombination is biased by supplying non-equimolar ratios of codon-varied oligonucleotides to the recombination composition. In this aspect, unlike certain other methods provided by the present invention, equimolar ratios of codon-varied oligonucleotides in a set of such oligonucleotides to be recombined are not used to produce a library of recombinant nucleic acids. Instead, ratios of particular oligonucleotides which correspond to the sequences of a selected member or selected set of members of the nucleic acids from which the codon-varied oligonucleotides are derived are selected by the practicioner. Non-equimolar ratios of codon-varied oligonucleotides may be achieved by, e.g., synthesizing disproportionate amounts of the relevant codon-varied oligonucleotides and/or providing disproportionate amounts to the composition of nucleic acids to be recombined.

The general strategy of tuning recombination by selecting oligonucleotide proportions is applicable to recombination of any two nucleic acids, whether of high or low sequence similarity. However, one advantage of this method when compared to other gene recombination approaches is that the overall sequence identity of two sequences to be blended can be lower. Further, sometimes only selected regions are recombined, making it possible to take available structural or functional data into account in specifying how the blended gene is constructed. As such, sequence space which cannot be created by other shuffling protocols is accessed by the blended gene and a higher percentage of active clones may be obtained if structural information is taken into consideration.

Codon-Varied Oligonucleotide Shuffling Targets

Virtually any nucleic acid can be recombined by the methods described in this disclosure. No attempt is made to identify the hundreds of thousands of known nucleic acids. As noted above, common sequence repositories for known proteins include GenBank®, Entrez®, EMBL, DDBJ and the NCBI. Other repositories can easily be identified by searching the internet.

One class of preferred targets for activation includes nucleic acids encoding therapeutic proteins, e.g., erythropoietin (EPO), insulin, peptide hormones, e.g., human growth hormone; growth factors and cytokines, e.g., epithelial Neutrophil Activating Peptide-78, GROα/MGSA, GROβ, GROγ, MIP-1α, MIP-1δ, MCP-1, epidermal growth factor, fibroblast growth factor, hepatocyte growth factor, insulin-like growth factor, the interferons, the interleukins, keratinocyte growth factor, leukemia inhibitory factor, oncostatin M, PD-ECSF, PDGF, pleiotropin, SCF, c-kit ligand, VEGF, G-CSF etc. Many of these proteins are commercially available (see, e.g., the Sigrna-Aldrich Co. 1999 *Biochemicals and Reagents* catalogue and price list), and the corresponding genes are well-known.

Another class of preferred targets are transcriptional and expression activators. Example transcriptional and expression activators include genes and proteins that modulate cell growth, differentiation, regulation, or the like. Expression and transcriptional activators are found in prokaryotes, viruses, and eukaryotes, including fungi, plants, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA. Expression activators include cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40/ CD40, VLA4/VCAM-1, ICAM-1/LFA-1, and hyalurin/ CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors, e.g., those for estrogen, progesterone, testosterone, aldosterone, the LDL receptor ligand and corticosterone.

Rnases, e.g., Onconase and EDN, are preferred targets for the synthetic methods herein, particularly those methods utilizing gene blending. One of skill will appreciate that both frog and human RNAses are known and are known to have a number of important pharmacological activities.

Similarly, proteins from infectious organisms for possible vaccine applications, described in more detail below, including infectious fungi, e.g., *Aspergillus, Candida* species; bacteria, particularly *E. coli*, which serves a model for pathogenic bacteria, as well as medically important bacteria such as *Staphylococci* (e.g., *aureus*), *Streptococci* (e.g., *pneumoniae*), *Clostridia* (e.g., *perfringens*), *Neisseria* (e.g., *gonorrhoea*), *Enterobacteriaceae* (e.g., *coli*), *Helicobacter* (e.g., *pylori*), *Vibrio* (e.g., *cholerae*), *Campylobacter* (e.g., *jejuni*), *Pseudomonas* (e.g., *aeruginosa*), *Haemophilus* (e.g., *influenzae*), *Bordetella* (e.g., *pertussis*), *Mycoplasma* (e.g., *pneumoniae*), *Ureaplasma* (e.g., *urealyticum*), *Legionella* (e.g., *pneumophilia*), Spirochetes (e.g., Treponema, Leptospira, and Borrelia), Mycobacteria (e.g., tuberculosis, smegmatis), *Actinomyces* (e.g., *israelii*), *Nocardia* (e.g., *asteroides*), *Chlamydia* (e.g., *trachomatis*), ickettsia, Coxiella, Ehrilichia, Rocholimaea, Brucella, Yersinia, Francisella, and Pasteurella; protozoa such as sporozoa (e.g., Plasmodia), rhizopods (e.g., Entamoeba) and flagellates (Trypanosoma, Leishmania, Trichomonas, Giardia, etc.); viruses such as (+) RNA viruses (examples include Poxviruses e.g., *vaccinia*; Picomaviruses, e.g. polio; Togaviruses, e.g., rubella; Flaviviruses, e.g., HCV; and Coronaviruses), (−) RNA viruses (examples include Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., especially HIV and HTLV, and certain DNA to RNA viruses, such as, Hepatitis B virus.

Other proteins relevant to non-medical uses, such as, inhibitors of transcription or toxins of crop pests, e.g., insects, fungi, weed plants, and the like, are also preferred targets for codon-varied oligonucleotide recombination. Industrially important enzymes, such as, monooxygenases (e.g., p450s), proteases, nucleases, and lipases are also preferred targets. As an example, subtilisin can be evolved by codon-varied oligonucleotides for homologous forms of the gene for subtilisin. Von der Osten et al., *J. Biotechnol.* 28:55–68 (1993) provide an example subtilisin coding nucleic acid. Proteins which aid in folding such as the chaperonins are also preferred targets.

Preferred known genes suitable for codon-varied oligonucleotide-mediated recombination also include the following: Alpha-1 antitrypsin, Angiostatin, Antihemolytic factor, Apolipoprotein, Apoprotein, Atrial natriuretic factor, Atrial natriuretic polypeptide, Atrial peptides, C-X-C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, Collagen, Colony stimulating factor (CSF), Complement factor 5a, Complement inhibitor, Complement receptor 1, Factor IX, Factor VII, Factor VIII, Factor X, Fibrinogen, Fibronectin, Glucocerebrosidase, Gonadotropin, Hedgehog proteins (e.g., Sonic, Indian, Desert), Hemoglobin (for blood substitute; for radiosensitization), Hirudin, Human serum albumin, Lactoferrin, Luciferase, Neurturin, Neutrophil inhibitory factor (NIF), Osteogenic protein, Parathyroid hormone, Protein A, Protein G, Relaxin, Renin, Salmon calcitonin, Salmon growth hormone, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Toxic shock syndrome toxin (TSST-1), Exfoliating toxins A and B, Pyrogenic exotoxins A, B, and C, and M arthritides mitogen, Superoxide dismutase, Thymosin alpha 1, Tissue plasminogen activator, Tumor necrosis factor beta (TNF beta), Tumor necrosis factor receptor (TNFR), Tumor necrosis factor-alpha (TNF alpha) and Urokinase.

Small proteins, such as, defensins (antifungal proteins of about 50 amino acids, EF40 (an anti fungal protein of 28 amino acids), peptide antibiotics, and peptide insecticidal proteins are also preferred targets and exist as families of related proteins. Nucleic acids encoding small proteins are particularly preferred targets, because conventional recombination methods provide only limited product sequence diversity. This is because conventional recombination methodology produces crossovers between homologous sequences about every 50–100 base pairs. This means that for very short recombination targets, cross-overs occur by standard techniques about once per molecule. In contrast, the codon-varied oligonucleotide recombination formats herein provide for recombination of small nucleic acids, as the practicioner selects any "cross-over" desired.

System Integration

As noted, supra, the initial codon-varied oligonucleotide sequence selection step of the invention can involve the alignment of nucleic acids using a computer and sequence alignment software. Other important integrated system components, however, can also provide for high-throughput screening assays, in addition to the coupling of such assays to oligonucleotide selection, synthesis and recombination.

The relevant assay will, naturally, depend on the application. There are many known assays for, e.g., proteins, receptors, and ligands. Formats include binding to immobilized components, cell or organismal viability, production of reporter compositions, and the like.

In the high throughput assays of the invention, it is possible to screen up to several thousand different recombination products in a single day. For example, each well of a microtiter plate can be used to run a separate assay, or, if concentration or incubation time effects are to be observed, every 5–10 wells can test a single product. Thus, a single standard microtiter plate can assay about 100 (e.g., 96) reactions. If 1536 well plates are used, then a single plate can easily assay from about 100 to approximately 1500 different reactions. It is possible to assay several different plates per day; assay screens for up to about 6,000–20,000 different assays (i.e., involving different nucleic acids, encoded proteins, concentrations, etc.) is possible using the integrated systems of the invention. More recently, microfluidic approaches to reagent manipulation have been developed, e.g., by Caliper Technologies (Mountain View, Calif.).

A number of well known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a scientist. Any of the above devices are suitable for use with the present invention, e.g., for high-throughput screening of molecules assembled from the various oligonucleotide sets described herein. The nature and implementation of modifications to these devices (if any) so that they can operate as discussed herein with reference to the integrated system will be apparent to persons skilled in the relevant art.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Optical images viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (Intel x86 or Pentium chip-compatible DOS™, OS2™ WINDOWS™, WINDOWS NT™ or WINDOWS95™ based machines), MACINTOSH™, or UNIX based (e.g., SUN™ work station) computers. One conventional system carries light from the assay device to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

Integrated systems for assay analysis in the present invention optionally include a digital computer with high-throughput liquid control software, image analysis software, data interpretation software, a robotic liquid control armature for transferring codon-varied oligonucleotide solutions or codon-varied oligonucleotide compositions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled assay component. The image scanner interfaces with the image analysis software to provide a measurement of probe label intensity.

These assay systems can also include integrated systems incorporating oligonucleotide selection elements, such as a computer, database with nucleic acid sequences of interest, sequence alignment software, and oligonucleotide selection software. Suitable alignment algorithms, e.g., BLAST and others are discussed, supra. However, sequence alignment can optionally be achieved manually. Once sequences to be synthesized are selected, they can be converted into lines of character string information in data sets in a computer corresponding to the desired codon-varied oligonucleotides to be obtained.

Additional software can be included, such as, components for ordering the selected oligonucleotides, and/or directing synthesis of oligonucleotides by an operably linked automated synthesizer. In this case, the character string information in the output of an integrated computer directs the robotic arm of the automated synthesizer to perform the steps necessary to synthesize the desired codon-varied oligonucleotide sequences.

Although, the integrated system elements of the invention optionally include any of the above components to facilitate high throughput recombination and selection. It will be appreciated that these high-throughput recombination elements can be in systems separate from those for performing selection assays, or as discussed, the two can be integrated.

Modifications can be made to the method and materials as hereinbefore described without departing from the spirit or scope of the invention as claimed, and the invention can be put to a number of different uses, including:

The use of an integrated system to select codon-varied oligonucleotides and to test recombined nucleic acids for activity, including in an iterative process.

An assay, kit or system utilizing a use of any one of the selection strategies, materials, components, methods or substrates hereinbefore described. Kits will optionally additionally comprise instructions for performing methods or assays, packaging materials, one or more containers which contain assay, device or system components, or the like.

In an additional aspect, the present invention provides kits embodying the methods and apparatus herein. Kits of the invention optionally comprise one or more of the following: (1) a recombination component as described herein; (2) instructions for practicing the methods described herein, and/or for operating the codon-varied oligonucleotide synthesis or recombined nucleic acid selection procedures herein; (3) one or more assay component(s); (4) a container for holding nucleic acids or enzymes, other nucleic acids, transgenic plants, animals, cells, or the like and, (5) packaging materials.

In a further aspect, the present invention provides for the use of any component or kit herein, for the practice of any method or assay herein, and/or for the use of any apparatus or kit to practice any assay or method herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were individually so denoted.

What is claimed is:

1. A method of providing a population of recombined nucleic acids, the method comprising:

(i) providing a population of oligonucleotides comprising at least one set of codon-varied oligonucleotides, wherein at least one member of the set of codon-varied oligonucleotides is chemically synthesized using at least trinucleotide sequences and wherein two or more members of the population comprise overlapping oligonucleotides;

(ii) hybridizing at least two of the overlapping oligonucleotides to each other to provide a population of hybridized overlapping oligonucleotides, which population of hybridized overlapping oligonucleotides comprises at least one codon-varied oligonucleotide; and, (iii) elongating members of the population of hybridized overlapping oligonucleotides, thereby providing the population of recombined nucleic acids.

2. The method of claim 1, further comprising selecting at least first and second nucleic acids to be recombined, wherein the set of codon-varied oligonucleotides comprises a plurality of codon-varied nucleic acids which correspond to the first and second nucleic acids.

3. The method of claim 2, wherein the first and second nucleic acids are homologous.

4. The method of claim 2, wherein the first and second nucleic acids are non-homologous.

5. The method of claim 1, wherein the providing step comprises trinucleotide synthesis comprising:

(a) providing a substrate sequence having a 5' terminus and at least one base, the 5' terminus and at least one base having protecting groups thereon;

(b) removing the 5' protecting group of the substrate sequence to provide a 5' deprotected substrate sequence;

(c) coupling the 5' deprotected substrate sequence with a selected trinucleotide phosphoramidite sequence having a 3' terminus, a 5' terminus, and three base groups, the 3' terminus, the 5' prime terminus, and the three base groups having protecting groups thereon, thereby yielding an extended oligonucleotide sequence; and, (d) repeating steps (b) and (c), wherein the extended oligonucleotide sequence yielded by each repeated step (c) becomes the substrate sequence of the next repeated step (b) until a desired codon-varied oligonucleotide is obtained.

6. The method of claim 1, wherein the providing step comprises trinucleotide synthesis performed in an automated synthesizer which automatically performs the steps of:

(a) providing a substrate sequence having a 5' terminus and at least one base, the 5' terminus and at least one base having protecting groups thereon;

(b) removing the 5' protecting group of the substrate sequence to provide a 5' deprotected substrate sequence;

(c) coupling the 5' deprotected substrate sequence with a selected trinucleotide phosphoramidite sequence having a 3' terminus, a 5' terminus, and three base groups, the 3' terminus, the 5' prime terminus, and the three base groups having protecting groups thereon, thereby yielding an extended oligonucleotide sequence; and, (d) repeating steps (b) and (c), wherein the extended oligonucleotide sequence yielded by each repeated step (c) becomes the substrate sequence of the next step (b) until a desired codon-varied oligonucleotide is obtained.

7. The method of claim 6, the method further comprising inputting character string information into the automatic synthesizer corresponding to the desired codon-varied oligonucleotides to be obtained.

8. The method of claim 7, wherein the character string information corresponds to two or more nucleic acids to be recombined.

9. The method of claim 1, wherein the providing step comprises providing a substrate sequence having a 5' terminus and at least one base, the 5' terminus and at least one base having protecting groups thereon, the substrate sequence further comprising a 3' end that is covalently attached to a solid support.

10. The method of claim 1, wherein the providing step comprises coupling together one or more of: mononucleotides, trinucleotide phosphoramidite sequences, and oligonucleotides.

11. The method of claim 1, wherein the providing step comprises split-pool synthesis comprising:

(a) providing substrate sequences, each having a 5' terminus and at least one base, the 5' terminus and at least one base having protecting groups thereon;

(b) removing the 5' protecting groups of the substrate sequences to provide 5' deprotected substrate sequences;

(c) coupling the 5' deprotected substrate sequences with a population of a selected trinucleotide phosphoramidite sequence, each having a 3' terminus, a 5' terminus, and three base groups, the 3' terminus, the 5' terminus, and the three base groups having protecting groups thereon, thereby yielding extended oligonucleotide sequences;

(d) repeating steps (b) and (c), wherein the extended oligonucleotide sequences yielded by each step (c) become the substrate sequences of the next step (b), until extended intermediate oligonucleotide sequences are produced;

(e) splitting the extended intermediate oligonucleotide sequences into two or more separate pools;

(f) removing the 5' protecting groups of the extended intermediate oligonucleotide sequences to provide 5' deprotected extended intermediate oligonucleotide sequences in the two or more separate pools;

(g) coupling the 5' deprotected extended intermediate oligonucleotide sequences with one or more selected mononucleotides, trinucleotide phosporamidite sequences, or oligonucleotides in the two or more separate pools, thereby yielding further extended intermediate oligonucleotide sequences;

(h) pooling the further extended intermediate oligonucleotide sequences from the two or more separate pools into a single pool; and, (i) repeating steps (b) through (h), wherein the further extended intermediate oligonucleotide sequences in the single pool of each step (h) become the substrate sequences of the next step (b), until desired codon-varied oligonucleotides are obtained.

12. The method of claim 11, further comprising selecting at least first and second nucleic acids to be recombined, wherein the set of codon-varied oligonucleotides comprises a plurality of codon-varied nucleic acids which correspond to the first and second nucleic acids wherein the first and second nucleic acids are non-homologous and are synthesized using the split-pool synthesis format.

13. The method of claim 12, wherein the non-homologous first and second nucleic acids are less than 90 percent identical.

14. The method of claim 13, wherein the split-pool synthesis format is module-based with a smallest module being a single trinucleotide in length and a larger module being at least 15 nucleotides in length.

15. The method of claim 1, wherein the providing step comprises split-pool synthesis performed in an automated synthesizer which automatically performs the steps of:

(a) providing substrate sequences having a 5' terminus and at least one base, the 5' terminus and at least one base having protecting groups thereon;

(b) removing the 5' protecting groups of the substrate sequences to provide 5' deprotected substrate sequences;

(c) coupling the 5' deprotected substrate sequences with a population of a selected trinucleotide phosphoramidite sequence having a 3' terminus, a 5' terminus, and three base groups, the 3' terminus, the 5' terminus, and the three base groups having protecting groups thereon, thereby yielding extended oligonucleotide sequences;

(d) repeating steps (b) and (c), wherein the extended oligonucleotide sequences yielded by each step (c) become the substrate sequences of the next step (b), until extended intermediate oligonucleotide sequences are provided;

(e) splitting the extended intermediate oligonucleotide sequences into two or more separate pools;

(f) removing the 5' protecting groups of the extended intermediate oligonucleotide sequences to provide 5' deprotected extended intermediate oligonucleotide sequences in the two or more separate pools;

(g) coupling the 5' deprotected extended intermediate oligonucleotide sequences with one or more selected mononucleotides, trinucleotide phosporamidite sequences, or oligonucleotides in the two or more separate pools, thereby yielding further extended intermediate oligonucleotide sequences;

(h) pooling the further extended intermediate oligonucleotide sequences from the two or more separate pools into a single pool; and, (i) repeating steps (b) through (h), wherein the further extended intermediate oligonucleotide sequences in the single pool of each step (h) become the substrate sequences of the next step (b), until desired codon-varied oligonucleotides are obtained.

16. The method of claim 15, further comprising selecting at least first and second nucleic acids to be recombined, wherein the set of codon-varied oligonucleotides comprises a plurality of codon-varied nucleic acids which correspond to the first and second nucleic acids wherein the first and second nucleic acids are non-homologous and are synthesized using the split-pool synthesis format performed in an automated synthesizer.

17. The method of claim 16, wherein the non-homologous first and second nucleic acids are less than 90 percent identical.

18. The method of claim 17, wherein the split-pool synthesis format performed in an automated synthesizer is module-based with a smallest module being a single trinucleotide in length and a larger module being at least 15 nucleotides in length.

19. The method of claim 15, the method further comprising inputting character string information into the automatic synthesizer corresponding to the desired codon-varied oligonucleotides to be obtained.

20. The method of claim 19, wherein the character string information corresponds to two or more nucleic acids to be recombined.

21. The method of claim 15, wherein the providing step further comprises providing a substrate sequence having a 3' terminus covalently attached to a solid support.

22. The method of claim 1, wherein the hybridizing step occurs in vitro.

23. The method of claim 1, wherein the hybridizing step occurs in vivo.

24. The method of claim 1, wherein (iii) comprises elongating the one or more members of the population of hybridized overlapping codon-varied oligonucleotides with a polymerase.

25. The method of claim 24, wherein the polymerase is a thermostable polymerase.

26. The method of claim 1, the method further comprising:
   denaturing the population of recombined nucleic acids to provide a set of denatured recombined nucleic acids;
   re-hybridizing at least one member of the set of denatured recombined nucleic acids to at least one other member of the set of denatured recombined nucleic acids to provide a population of re-hybridized recombined nucleic acids;
   elongating one or more members of the population of rehybridized recombined nucleic acids to provide a population of further recombined nucleic acids; and,
   selecting at least one member of the population of further recombined nucleic acids for at least one desired trait or property.

27. The method of claim 1, the method further comprising the steps of:
   denaturing the population of recombined nucleic acids to provide a set of denatured recombined nucleic acids;
   re-hybridizing at least one member of the set of denatured recombined nucleic acids to at least one other member of the set of denatured recombined nucleic acids to provide a population of re-hybridized recombined nucleic acids;
   elongating one or more members of the population of re-hybridized recombined nucleic acids to provide a population of further recombined nucleic acids; and,
   repeating the denaturing, re-hybridizing and elongating steps at least once.

28. The method of claim 27, further comprising selecting at least one member of the population of further recombined nucleic acids for at least one desired trait or property.

29. The method of claim 27, wherein a plurality of members of the population of recombined nucleic acids are selected for a desired trait or property to provide first round selected nucleic acids, the method further comprising:
   hybridizing at least one member of a second set of overlapping codon-varied oligonucleotides to at least one other member of the second set of overlapping codon-varied oligonucleotides to provide a second population of hybridized overlapping codon-varied oligonucleotides, which second set of overlapping codon-varied oligonucleotides is derived from the first round selected nucleic acids; and,
   elongating one or more members of the second population of hybridized overlapping codon-varied oligonucleotides to provide a second population of further recombined nucleic acids.

30. The method of claim 29, further comprising sequencing the first round selected nucleic acids, wherein the second set of overlapping codon-varied oligonucleotides is derived from the first round selected nucleic acids by aligning sequences of the first round selected nucleic acids to one another to identify regions of similarity and regions of diversity in the first round selected nucleic acids, and synthesizing the second set of overlapping codon-varied oligonucleotides to comprise a plurality of oligonucleotides, each of which comprise subsequences corresponding to at least one region of diversity.

31. The method of claim 29, wherein the first round selected nucleic acids encode polypeptides of about 50 amino acids or less.

32. The method of claim 29, wherein the second set of overlapping codon-varied oligonucleotides comprises a plurality of oligonucleotide member types which comprise consensus region subsequences derived from a plurality of the first round selected nucleic acids.

33. The method of claim 1, further comprising selecting at least one member of the population of recombined nucleic acids for at least one desired trait or property.

34. The method of claim 1, wherein the set of overlapping codon-varied oligonucleotides comprises a plurality of oligonucleotide member types which comprise consensus region subsequences derived from a plurality of homologous target nucleic acids.

35. The method of claim 1, wherein the set of overlapping codon-varied oligonucleotides comprises at least 3 oligonucleotide member types.

36. The method of claim 35, wherein the set of overlapping codon-varied oligonucleotides comprises at least 5 oligonucleotide member types.

37. The method of claim 36, wherein the set of overlapping codon-varied oligonucleotides comprises at least 10 oligonucleotide member types.

38. The method of claim 1, wherein the set of overlapping codon-varied oligonucleotides comprises a plurality of homologous oligonucleotide member types, wherein the homologous oligonucleotide member types are present in equimolar amounts.

39. The method of claim 1, wherein the set of overlapping codon-varied oligonucleotides comprises a plurality of homologous oligonucleotide member types, wherein the homologous oligonucleotide member types are present in non-equimolar amounts.

* * * * *